US012661127B1

(12) United States Patent     (10) Patent No.:   US 12,661,127 B1

Aarsheim et al.     (45) Date of Patent:   Jun. 23, 2026

---

(54) OSTEOTOME WITH DISPOSABLE BLADE

(71) Applicant: Q SURGICAL, LLC, Sausalito, CA (US)

(72) Inventors: Will R. Aarsheim, Sausalito, CA (US); Larry D. Harwood, Fife, WA (US)

(73) Assignee: Q SURGICAL, LLC, Sausalito, CA (US)

( * ) Notice: Subject to any disclaimer, the term of this patent is extended or adjusted under 35 U.S.C. 154(b) by 160 days.

(21) Appl. No.: 18/453,522

(22) Filed: Aug. 22, 2023

Related U.S. Application Data

(60) Provisional application No. 63/400,115, filed on Aug. 23, 2022.

(51) Int. Cl.
    *A61B 17/16*     (2006.01)

(52) U.S. Cl.
    CPC ...... *A61B 17/1604* (2013.01); *A61B 17/1613* (2013.01)

(58) Field of Classification Search
    CPC ............... B25D 3/00; B25D 2250/051; A61B 17/16–1697
    USPC ..................... 403/200; 30/167, 534; 606/100
    See application file for complete search history.

(56) References Cited

U.S. PATENT DOCUMENTS

| | | | | | |
|---|---|---|---|---|---|
| 1,082,379 | A | * | 12/1913 | West | B25D 3/00 |
| | | | | | 30/167 |
| 2,406,983 | A | * | 9/1946 | Anderson | B26B 21/52 |
| | | | | | 30/534 |

| | | | | | |
|---|---|---|---|---|---|
| 3,334,624 | A | * | 8/1967 | Schneider | A61B 17/921 |
| | | | | | 606/100 |
| 3,964,163 | A | * | 6/1976 | Russo | A61B 17/144 |
| | | | | | 606/177 |
| 4,069,586 | A | * | 1/1978 | Skelton | B25D 5/00 |
| | | | | | 30/360 |

(Continued)

FOREIGN PATENT DOCUMENTS

| | | |
|---|---|---|
| AU | 2020204213 A1 | 7/2020 |
| CN | 102113903 A | 7/2011 |

(Continued)

OTHER PUBLICATIONS

European Patent Office—Espacenet Search Results for "osteotome + replaceable" (Nov. 24, 2021).

(Continued)

*Primary Examiner* — Matthew J Lawson

(74) *Attorney, Agent, or Firm* — R. Reams Goodloe, Jr.

(57)        ABSTRACT

An osteotome with replaceable blades. The osteotome includes a replaceable blade portion and a handle portion. The blade portion is detachably affixed to the handle portion. Replaceable blade portions are affixed to the reusable handle portion. The blade portions have a tool edge portion and blade shaft portion. The blade shaft portion extends between the base and a proximal end having an externally threaded portion. The handle portion has a hand grip portion and a handle shaft portion. A threaded coupler is provided. The proximal end of the blade shaft portion and the distal end of the handle shaft portion include complementary interlocking end pieces, which prevent rotation therebetween. An interior shaft and strike plate in the handle portion assure steel-to-steel contact from the strike plate to the sharp distal end.

23 Claims, 6 Drawing Sheets

(56) References Cited

U.S. PATENT DOCUMENTS

| | | | | |
|---|---|---|---|---|
| 4,624,323 A * | 11/1986 | Burrola | ............... | B25B 23/16 72/457 |
| 4,823,781 A * | 4/1989 | Buchanan | .......... | A61B 17/6408 606/54 |
| 4,844,070 A * | 7/1989 | Dee | ............... | A61B 17/3213 279/42 |
| D342,313 S | 12/1993 | Hood | | |
| 5,370,192 A * | 12/1994 | Evinger | ............... | B25D 1/16 173/132 |
| 5,461,900 A * | 10/1995 | Gutierrez | ............. | B21D 1/06 81/463 |
| 6,769,182 B1 * | 8/2004 | McCabe | ............. | B25D 3/00 81/463 |
| 7,191,685 B2 * | 3/2007 | Lowther | ............... | B25D 1/16 81/463 |
| D793,556 S | 8/2017 | Sweitzer | | |
| 10,595,879 B1 | 3/2020 | Litwak | | |
| D931,448 S | 9/2021 | Taylor | | |
| D933,215 S | 10/2021 | Gloess | | |
| D990,680 S | 6/2023 | Wright | | |
| D995,777 S | 8/2023 | Sweitzer | | |
| D997,354 S | 8/2023 | Wright | | |
| D1,005,487 S | 11/2023 | Niver | | |
| D1,006,226 S | 11/2023 | Goode | | |
| D1,009,266 S | 12/2023 | Maruo | | |
| D1,029,258 S | 5/2024 | Stroh | | |
| D1,032,838 S | 6/2024 | Ahn | | |
| 2008/0189957 A1 * | 8/2008 | Kasper | ............... | B25D 3/00 30/167 |
| 2010/0237058 A1 * | 9/2010 | Evans | ............... | B23K 3/08 228/55 |
| 2012/0255180 A1 * | 10/2012 | Powers | ............... | B25D 3/00 30/167.1 |
| 2014/0194939 A1 * | 7/2014 | Seelig | ............... | A61B 17/7086 606/86 A |
| 2015/0039037 A1 * | 2/2015 | Donner | ............. | A61B 17/7055 606/85 |
| 2020/0305892 A1 | 10/2020 | Cao | | |
| 2021/0053200 A1 * | 2/2021 | Hatamochi | ............ | B25D 17/08 |
| 2023/0013129 A1 * | 1/2023 | Schweitzer | ........ | A61B 17/1604 |
| 2023/0346393 A1 | 11/2023 | Braxton | | |
| 2024/0277369 A1 * | 8/2024 | Zinnanti | ............... | A61B 17/29 |

FOREIGN PATENT DOCUMENTS

| | | |
|---|---|---|
| KR | 10-1565118 | 10/2015 |
| SU | 1660688 A1 | 7/1991 |
| UA | 6446 | 5/2005 |

OTHER PUBLICATIONS

Life Instrument Corporation—Life Instruments—Orthopedic Instruments. Catalogue (2016-00-00) (40pgs).

* cited by examiner

OSTEOTOME WITH DISPOSABLE BLADE

REFERENCE TO RELATED PATENT APPLICATIONS

This application claims priority from prior U.S. Provisional Patent Application Ser. No. 63/400,115, filed Aug. 23, 2022, entitled OSTEOTOME WITH DISPOSABLE BLADE, the disclosure of which is incorporated herein in its entirety, including the specification, drawing, and claims, by this reference.

STATEMENT OF GOVERNMENT INTEREST

Not Applicable.

COPYRIGHT RIGHTS IN THE DRAWING

TECHNICAL FIELD

My invention relates to surgical instrument systems involving hand tools for cutting bone, specifically including but not limited to osteotomes.

BACKGROUND OF THE INVENTION

Spine surgery almost always involves removing some amount of bone. There usually significant risk involved in any bone removal, and especially in spinal surgery, since bone portions to be removed are almost always in close proximity to critical structures like nerves, or the spinal cord, or the dura which covers the spinal cord and holds therein the cerebral spinal fluid. As known amongst spinal surgeons, there are various prior art devices available which may be used to remove portions of bones during spinal surgery. As an example, a device known as a Kerrison (for example under the brand names Kwik Kleen Kerrison®, or Symmetry Sharp Kerrison® both trademarks now registered by Specialty Surgical Instrumentation, Inc., or with similar instruments by other vendors), is frequently used to remove small bites of bone. They are often used for removing bone portions that are about one (1) to about five (5) millimeter in width. And, an osteotome is frequently used to cut through bone. All of such prior art products have benefits, but have risks of injury, depending upon the speed of bone removal, as well as the size and type of bone cut being undertaken.

Importantly, the various bone removal tools currently available have different useful life, depending primarily on sharpness retention of the blade. In must be noted that drills may be used for bone removal, but drill bits are disposable, and thus can be easily and economically replaced with sharp new drill bits. Over time, as a result of multiple uses in hospital settings, Kerrisons and osteotomes are dulled by contact with bone. However, currently available Kerrisons and osteotomes are not provided as disposable tools.

In a prior art osteotome design which provided a disposable blade, found in Ukraine Specification for a Declarative Patent for a Utility Model, No. UA 6446 U, by Arkadiiovych et al., dated May 16, 2005, the design utilized a fastening screw oriented transverse to the longitudinal axis of the device for attachment of a replaceable blade. Such a design may result in undesirable interference between the fastening screw (or adjacent structure of the device) and adjacent tissue of a patient when the device is in use, as can be appreciated from a view of FIG. 2 of that utility model. Further, use of a swallow tail socket (see FIG. 3 of that utility model) for receiving the tail part of the replaceable blade presents recesses which may be difficult to fully clean and sterilize between uses. Further, it is unclear whether a force applied to a striking plate, such as by a hammer or mallet, might result in slippage between the screw and the blade when force is applied against the proximal end of the blade, since FIG. 6 of that utility model clearly reveals that the blade design is configured to accept such slippage. Any change of longitudinal dimension of an osteotome during use would be undesirable during a surgical procedure, since such slippage would decrease a user's ability to rely on the consistency between force being applied, and the length of cut achieved in a bone.

Thus, it would be desirable if a new design for an osteotome were available in which the force applied to the handle resulted in reliable movement of a sharp distal end of a blade portion into a bone. And it would extremely desirable if a blade could be economically replaced at every new surgery. However, at the present, such a practice would be cost prohibitive.

Some Objects of the Invention, Advantages and Novel Features

From the foregoing, it will be apparent that an object of the present invention resides in the provision of a reliable and replaceable blade portion of an osteotome, which is simple, straightforward, and which is sized and shaped for selection of a tool edge portion of suitable width for ease of use in spinal surgery or other surgical procedures requiring bone removal.

Another objective of the device disclosed and claimed herein is to provide a design for an osteotome in which a sharp cutting surface may be assured for use each time a surgical procedure is undertaken.

Another objective is to provide an osteotome in which a blade portion may be disposed after use, with low replacement cost.

A related objective is to provide a reusable handle for an osteotome, wherein a striking plate and grip may be sterilized for reuse with a selected new blade portion.

A further related objective is to provide an osteotome design having replaceable blade portions, wherein the reusable handle portion is easily and reliably sterilizable for reuse in a clean, sterile surgical environment.

A yet further related objective is to provide a reusable handle portion for a surgical tool system that may be utilized with any one of a set of blade portions, wherein the blade portion may be selected having a desired end geometry, and desired width at the sharp distal end of the working tool edge portion of the blade portion.

A related objective is to provide a replaceable end effector for use in a surgical instrument system, where a new end effector may be easily, reliably, and inexpensively affixed to a handle portion which has been sterilized for reuse.

Another related objective is to provide a disposable osteotome design which can be easily assembled and disassembled by surgeons and their operating room support personnel, without need for tools.

Finally, another important objective is to provide a high quality osteotome surgical system design which can be conveniently and easily manufactured with conventional manufacturing processes, so that manufacturing costs are minimized, to minimize usage and blade portion replacement costs, even when regularly disposing of blade portions which have been utilized in an operation for removal of bone.

An advantage of the novel osteotome design disclosed herein is that a very sharp cutting edge on the distal end of the blade portion is assured for each surgical procedure, since a new, sharp edged blade portion can be installed with a reused handle portion before each surgical procedure.

Another advantage of the novel osteotome design provided herein is that, if necessary, blade portions may be easily and readily changed, to provide a selection from different widths of selected blade portions, as may be required for particular bone removal requirements.

Further, in an embodiment, the novel osteotome design provided herein provides solid steel-to-steel contact within a coupler, as well as solid steel-to-steel contact along the entire longitudinal axis, so that force applied to a striker plate on the proximal end of the handle portion is reliably transmitted directly to the sharp distal end of the tool edge portion of the blade portion.

Other objects, features, and additional advantages of my osteotome design as disclosed herein, as well as use of the design for other surgical instrument systems, will become apparent to those skilled in the art, from the foregoing as well as from the detailed specification which follows, and from the appended claims in conjunction with the accompanying figures of the drawing.

SUMMARY

A novel osteotome design is provided. The osteotome design includes a blade portion which has a tool edge portion and a blade shaft portion. The tool edge portion has a longitudinal base which extends outward to a sharp distal end. The sharp distal end has a selected width W, where W may be in the range of from about two (2) millimeters to about thirty one point seven five (31.75) millimeters. The blade shaft portion extends between a proximal end of the longitudinally extending base and a first proximal end of the blade shaft portion. An externally threaded portion is provided on the blade shaft portion adjacent the first proximal end.

The osteotome design also includes a handle portion. The handle portion includes a hand grip portion and a handle shaft portion. In an embodiment, a strike plate is provided at the proximal end of the hand grip portion. The handle shaft portion extends between the hand grip portion and a first distal end. In an embodiment, an interior shaft is provided between the strike plate and the proximal end of the handle shaft portion. In an embodiment, the strike plate may be welded to the interior shaft. In an embodiment, the interior shaft may be welded to the proximal end of the handle shaft portion, so that a continuous solid metal (normally surgical grade stainless steel) connection is provided from the strike plate to the distal end of the handle shaft portion. In an embodiment, a retainer is provided at or near the first distal end of the handle shaft portion. In an embodiment, the retainer may be provided as a hoop that is configured to outwardly protrude from the handle shaft portion. In an embodiment, the first proximal end of the blade shaft portion may include a female end piece. In an embodiment, the first distal end of the handle shaft portion may include a male end piece. In an embodiment, the just mentioned male and female end pieces may be designed for interlocking engagement. In an embodiment, the just mentioned male and female end pieces may be configured and interlocked so as to prevent rotation between the handle portion and the blade portion.

The osteotome design may also include a coupler which is used to join the handle portion and the blade portion. In an embodiment, the coupler may be provided configured at least partially as a tubular cylindrical structure, having (a) a cylindrical portion with an interior surface that is at least partially threaded, and (b) a retaining portion. The coupler is sized and shaped for sliding engagement along at least a portion of the handle shaft portion. In an embodiment, the coupler may be retained on the handle shaft portion by interference between the retainer and the retaining portion, wherein the retainer prevents the retaining portion of the coupler (and thus retains the coupler) from travel outward beyond retainer on the handle shaft portion. The coupler may be sized and shaped for threaded engagement with the externally threaded portion of the blade shaft portion. Upon tightening, the coupler thereby secures the handle portion to the blade portion.

In an embodiment, the novel osteotome design disclosed herein may provide a solid steel (usually, surgical grade stainless steel) pathway from strike plate all the way to the sharp distal end of the blade portion. Thus, in an embodiment, an osteotome may be configured to provide a center-line force pathway from strike plate to the sharp distal end of the blade portion.

Thus, in various embodiments, the designs provided herein provide a replaceable end effector for use in a surgical instrument system. Replacement blade portions may be provided in duplicates having an identical cutting width W. Or, replacement blade portions may be provided in kits having a plurality of blade portions where the cutting width W of the sharp distal end of the various blade portions may include various widths, particularly in the range of from about two (2) millimeters to about thirty one point seven five (31.75) millimeters.

In an embodiment, a surgical instrument kit may be provided, including at least one handle portion, constructed for reuse, and a plurality of blade portions at least some of which are suitable for disposal after a single use. In an embodiment, the plurality of blade portions may include blade portions having chisel blade designs. In an embodiment, the plurality of blade portions may include blade portions having osteotome blade designs.

BRIEF DESCRIPTION OF THE DRAWING

The present invention(s) will be described by way of exemplary embodiments, using for illustration the accompanying drawing in which like reference numerals in the various drawing figures denote like elements, and in which:

FIG. 1 is a perspective view of an embodiment for an assembled osteotome, showing use of a blade portion and a handle portion joined at a coupler.

Figures 2, 3:
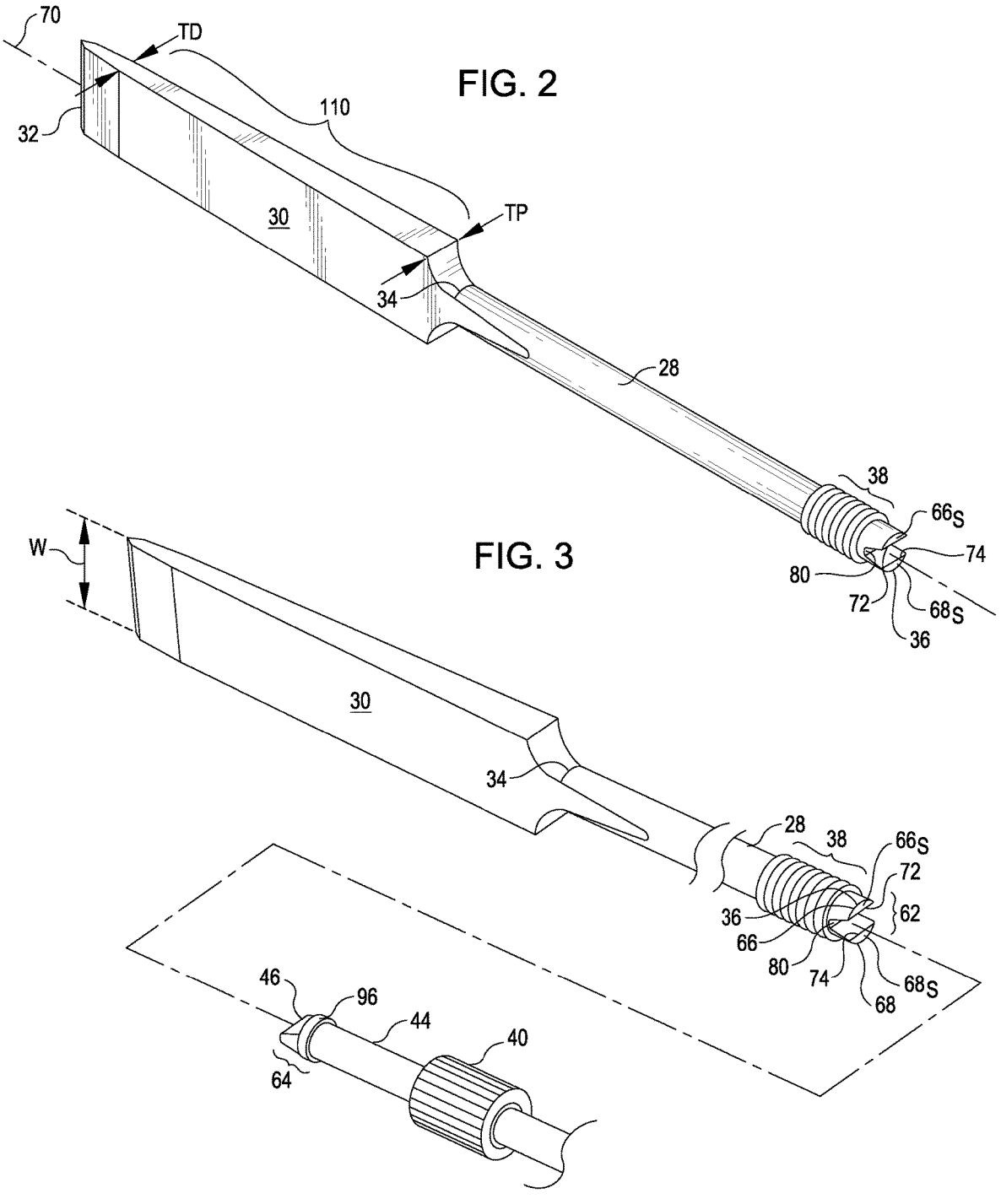
FIG. 2 is a perspective view of an embodiment for a blade portion of an osteotome, and which is separated from the handle portion, showing the use of a cylindrical blade shaft portion, with an exterior threaded portion near or at the proximal end thereof, as well as use of an interlocking end configuration which is configured for firm, stable interlocking engagement with a handle portion, as seen in FIG. 1 above, and in further detail in FIGS. 6 and 7 below.
FIG. 3 is a partial perspective view of an embodiment for a blade portion of an osteotome, also showing the end of a handle shaft portion, wherein the blade portion is separated from the handle shaft portion, and showing the use of a cylindrical blade shaft portion, with an exterior threaded portion near or at the proximal end thereof, as well as use of an interlocking end configuration on each of the blade shaft portion and the handle shaft portion, where the interlocking end configurations are designed for firm, stable interlocking engagement between the blade shaft portion and the handle shaft portion, as well as showing a retainer on the handle shaft portion, and showing the coupler used for securely joining the handle shaft portion to the blade shaft portion.

The foregoing figures, being merely exemplary, contain various elements that may be present or omitted from a final configuration for an embodiment of an osteotome system that uses a blade portion and a handle portion which are joined together for use. Internal materials, and in particular various materials from the striker plate center to the sharp distal end, may be provided in the form of surgical steel having a suitable stainless steel specification (e.g. 316L SS, or products meeting the ASTM F56 standard) as known by those of skill in the art. However, alternate materials may be provided that nevertheless provide solid and reliable contact and reaction along the longitudinal axis of the osteotome, to provide a reliable osteotome with replaceable blade portions, as described and claimed herein. Other variations in materials, or other sizes or shapes of components such as blade shapes or sizes, and materials of construction, may be provided and yet employ the principles described herein and as generally depicted in the drawing figures provided, and as more specifically called out in the claims set forth below. For example, while uses of stainless steel components suitable for surgical applications are suggested, other materials which meet end use requirements may be utilized.

Although various dimensions may be utilized by those of skill in the art in order to make and use the claimed invention, and there is no intention to limit the claimed invention to the use of sizes or shapes set out in the specification or referenced in the drawing figures, or more generally, to any of the dimensional data provided, all of which is exemplary rather than mandatory. Thus, an osteotome system with a separable blade portion and a handle portion may be provided in other shapes, and or in which components are sized up or down from any dimensions provided, or with parts provided in metric system sizes or in English system sizes, without affecting the scope of the appended claims. An attempt has been made to draw the figures in a way that illustrates at least those elements that are significant for an understanding of the exemplary surgical instrument system which may be used with various types of replaceable or disposable blade portions while reusing handle portions. Finally, for ease of reference, like features in various drawing figures may be described using like reference numerals, or other like references, without further mention thereof.

DETAILED DESCRIPTION

Figure 1:
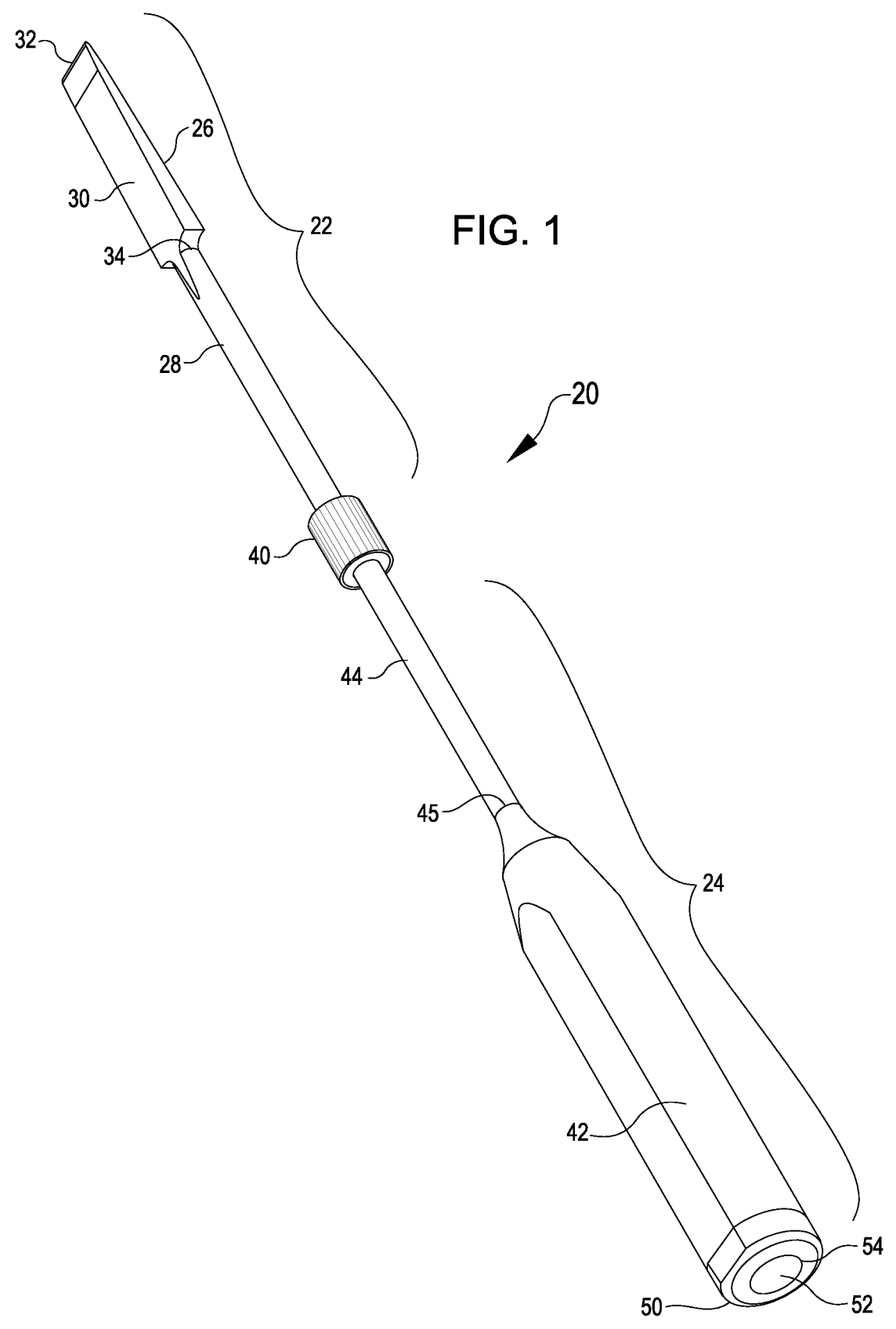

Attention is directed to FIG. 1 where a perspective view is provided of a novel osteotome 20 having a blade portion 22 and a handle portion 24, where the blade portion 22 and the handle portion 24 are separable components. The blade portion 22 has a tool edge portion 26 and a blade shaft portion 28. The tool edge portion 26 has a longitudinally extending base 30 extending outward to a sharp distal end 32. As better seen in FIG. 3, the blade shaft portion 28 extends between a proximal end 34 of the longitudinally extending base 30 and a first proximal end 36 of the blade shaft portion 28. At or adjacent the first proximal end 36 of the blade shaft portion 28, an externally threaded portion 38 may be provided. As shown in FIGS. 1 and 3, a coupler 40 may be used to securely join the separable blade portion 22 and handle portion 24.

Figures 4, 5, 6:
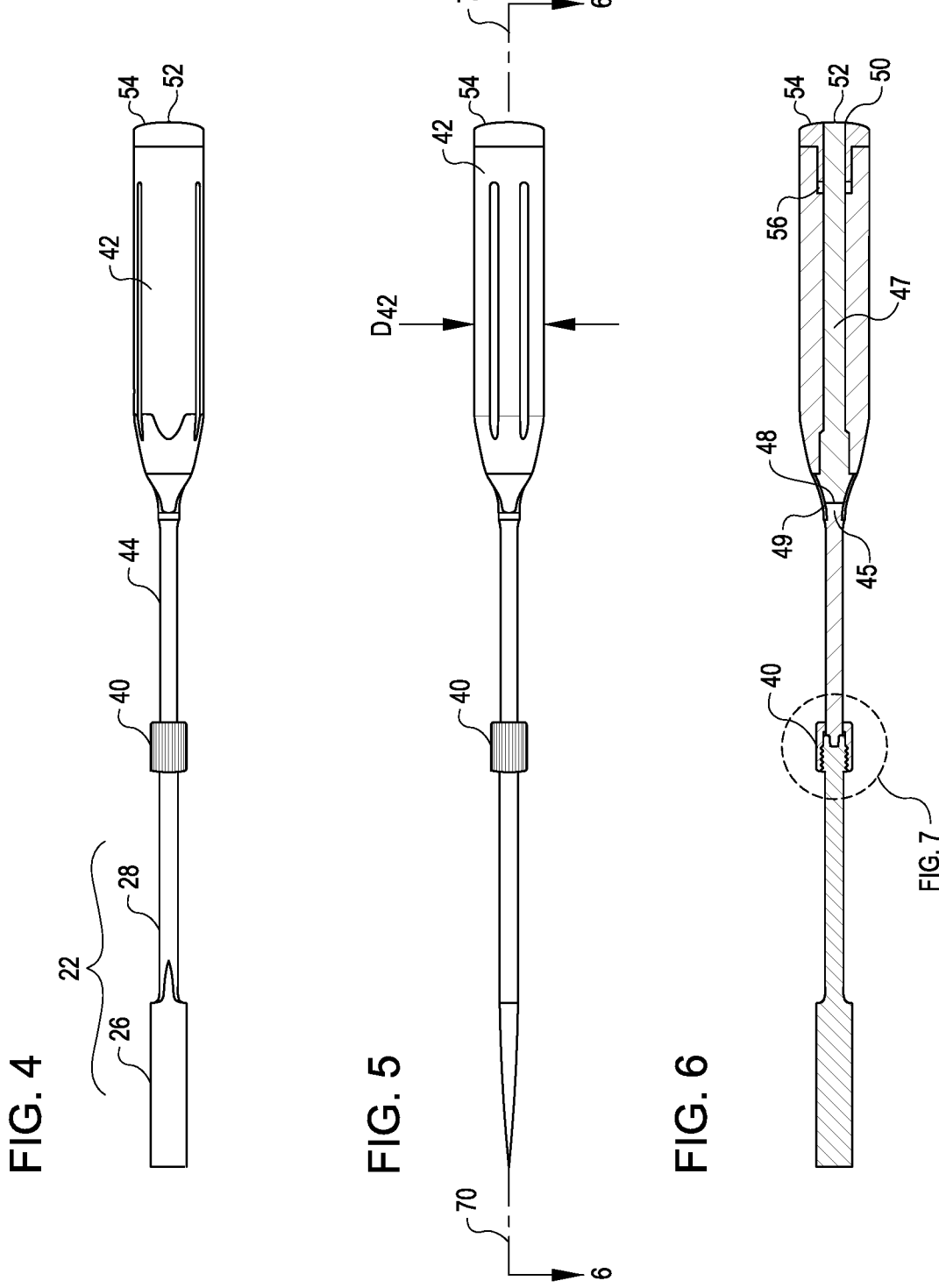
FIG. 4 is a plan view of an embodiment of for an osteotome having a disposable blade portion, taken looking down on the osteotome, showing the blade portion joined to the handle portion using a coupler.
FIG. 5 is a side elevation view of an embodiment for an osteotome having a disposable blade portion, as just illustrated in FIG. 4 above, taken looking at the side of the osteotome, showing the blade portion joined to the handle portion using a coupler, all aligned along a longitudinal axis from the striker plate on the handle portion to a sharp distal end of the tool edge portion of the blade portion.
FIG. 6 is a cross-sectional view, taken along line 6-6 of FIG. 5, showing the internal configuration of an embodiment for an osteotome having a disposable blade portion, showing the blade portion, the coupler that joins the blade portion and the handle portion, the handle shaft portion and the internal shaft in the handle portion (which may be joined by welding, after placement of the coupler in a working assembly), as well as the striker plate at the proximal end of the handle shaft portion (where the striker plate may be securely joined by weldment to the internal shaft), to reveal, in total, a solid steel structure running along a longitudinal axis between the striker plate on the proximal end of the handle portion all the way to the sharp distal end of the blade portion.
Figures 13, 14, 15:
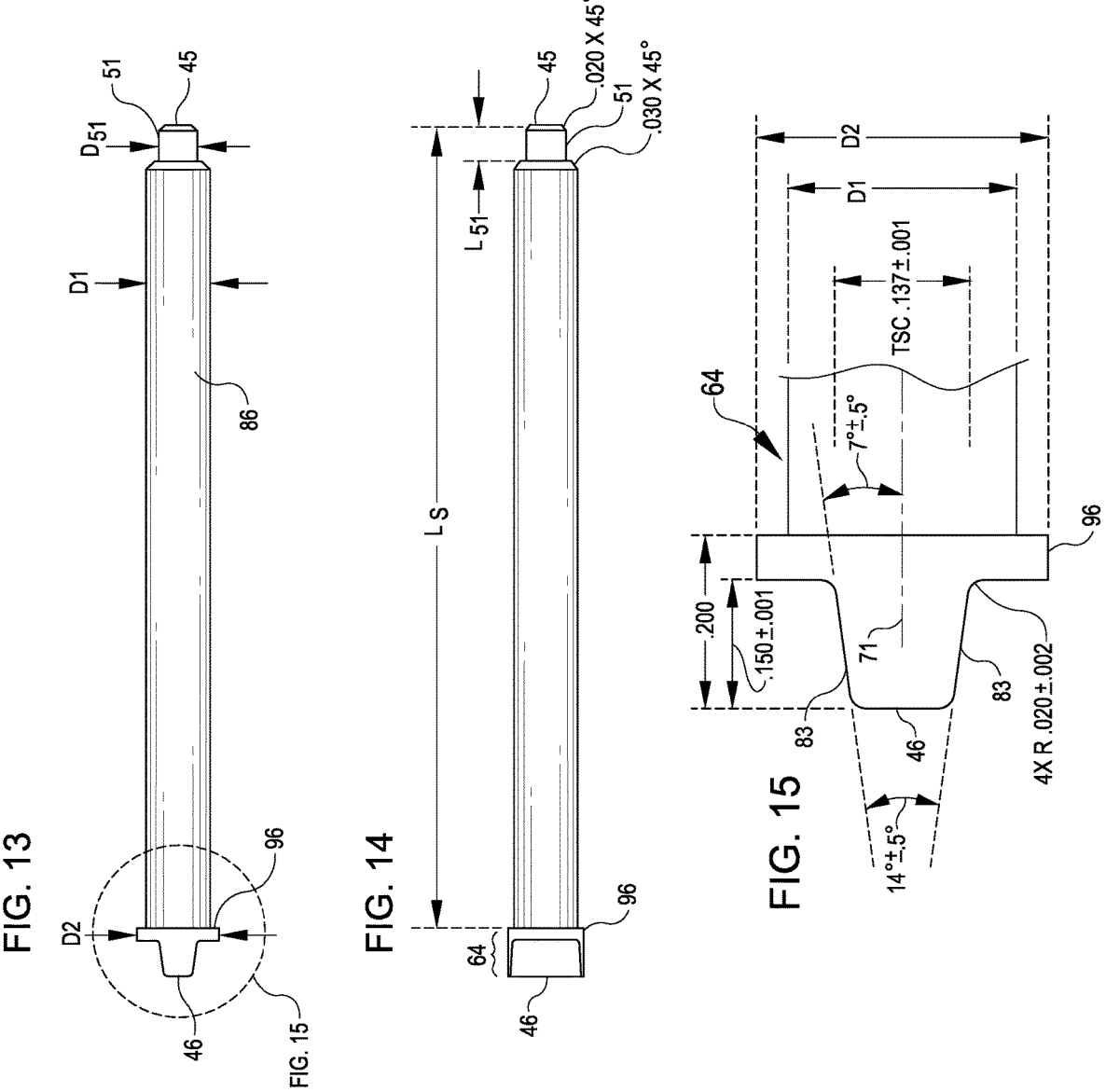
FIG. 13 is a side elevation view of an exemplary embodiment for a handle shaft portion, before it is secured (preferably by welding) to an interior shaft in the handle portion, showing a second end piece located in the first distal end of the handle shaft portion.
FIG. 14 is a plan view of exemplary embodiment for a handle shaft portion, before it is secured (preferably by welding) to an interior shaft in the handle portion, showing a second end piece located in the first distal end of the handle shaft portion.
FIG. 15 is a side elevation view of a second end piece, providing a detail 15-15 from FIG. 13 above, showing a second end piece which is located in the first distal end of the handle shaft portion, further providing details of construction which enable the handle shaft portion and the blade shaft portion to be secured together in a solid, steel-to-steel contact, and anti-rotation configuration.

As seen in FIG. 1, the handle portion 24 includes a hand grip portion 42 and a handle shaft portion 44. As seen in FIGS. 6, 13 and 14, the handle shaft portion 44 extends between a handle shaft proximal end 45 adjacent the hand grip portion 42 and a first distal end 46. As seen in FIG. 6, in an embodiment the hand grip portion 42 includes an interior shaft 47, which may include a socket 48 for receiving proximal end 45 of the handle shaft portion 44. In an embodiment, the proximal end 45 of the handle shaft portion 44 may be welded at socket 48 to the interior shaft 47 (see weldment 49), to assure a solid steel-to-steel connection therebetween. To facilitate assembly, the proximal end 45 may be provided having a short stub 51 of diameter $D_{51}$ and length $L_{51}$ where $D_{51}$ is less than diameter D1 of the handle shaft portion 44. In an embodiment, diameter $D_{51}$ may be about zero point one five zero (0.150) inches (about three point eight one (3.81) millimeters). In an embodiment, length $L_{51}$ may be about zero point one five zero (0.150) inches (about three point eight one (3.81) millimeters). In an embodiment, the handle shaft portion 44 may have an unassembled length LS, not including second end piece 64, of about three point two five (3.25) inches (about eighty two point fifty five (82.55) millimeters. In any event, it must be understood that the various dimensions provided herein are suggested only for an embodiment of a particular size, and that dimensions may be easily adjusted by those of skill in the art to accommodate various sizes, shapes, and styles of replaceable end effectors, whether they be osteotomes, chisels, or other tools as may be conveniently utilized using the concepts herein.

At the proximal end 50 of handle portion 24, the interior shaft 47 may extend proximally to an exposed strike end 52. The exposed strike end 52 may be surrounded by a strike plate 54, as seen in FIGS. 1 and 6. To assure rigidity and steel-to-steel connection, the exposed strike end 52 and the strike plate 54 may also be welded together at one or more locations (see weldment 56).

Figure 7:
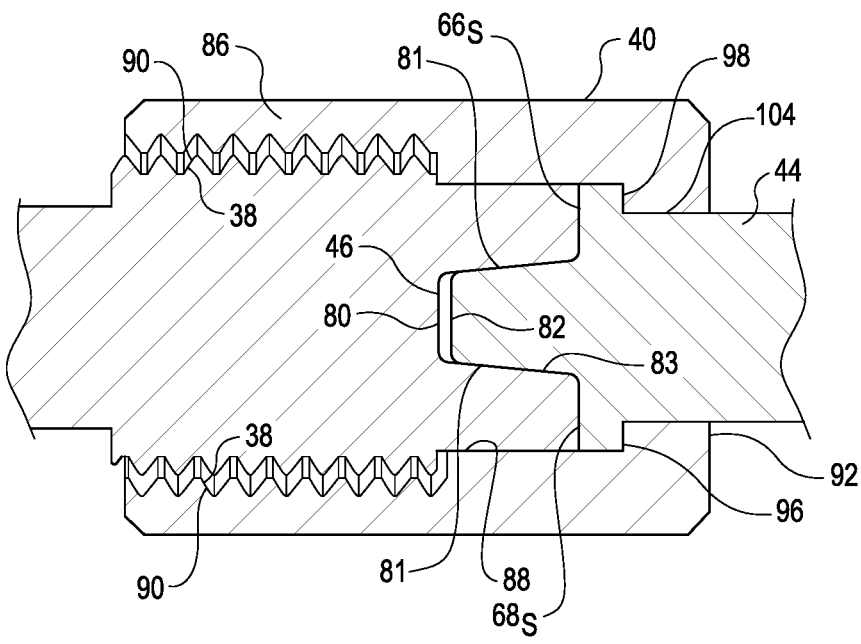
FIG. 7 is a vertical cross-section of an embodiment for a coupler, taken within detail 7-7 as shown in FIG. 12, showing a coupler that joins the handle shaft portion to the chisel shaft portion, where coupler is configured with cylindrical portion having an interior which is at least partially threaded, and a retaining portion, and wherein the coupler is sized and shaped for sliding engagement along at least a portion of the handle shaft portion, and wherein the coupler is retained on the handle shaft portion by interference between the retainer which prevents the retaining portion of the coupler to slide past the retainer, as well as showing how the coupler is sized and shaped for threaded engagement with the externally threaded portion of the blade shaft portion, and upon tightening thereby secures the handle portion to the blade portion.

As seen in FIGS. 2, 3, and 7, in an embodiment, the first proximal end 36 of the blade shaft portion 28 includes a first end piece 62. In an embodiment, the first distal end 46 of the handle shaft portion 44 is included in a second end piece 64, as seen in FIG. 14. In an embodiment, the first end piece 62 and the second end piece 64 (see FIG. 3) may be designed for interlocking engagement using a configuration which prevents rotation therebetween. In an embodiment, the first end piece 62 may include a pair of circular segments 66 and

68 with surfaces 66s and 68s respectively which are oriented transversely to a longitudinal axis 70 (see FIG. 5) of the blade shaft portion 28. The circular segments 66 and 68 have interior chords 72 and 74, respectively. A gullet 80 is located between circular segments 66 and 68, which in an embodiment may be defined between interior chords 72 and 74 (which may be radiused as indicted in FIG. 7), where the gullet 80 slopes inwardly along sidewalls 81 and extends distally along the longitudinal axis 70 of the blade shaft portion 28, In an embodiment, the second end piece 64 on the handle shaft portion 44 includes a generally U-shaped protrusion 82, with sloping sidewalls 83, and which is sized and shaped for close fitting engagement within gullet 80 (and mating engagement between sidewalls 81 and sloping sidewalls 83), and disposed for secure interlocking engagement with the gullet 80 in the first end piece 62. Thus, the generally U-shaped protrusion 82 slopes inwardly along sidewalls 83 and extends distally to the first distal end 46, as seen in FIGS. 7 and 15. As noted in FIG. 15, in an embodiment, the inwardly sloping sidewalls 83 may be provided at an angle of from about two degrees (2°) to about twelve degrees (12°) from a longitudinal axis 71 of the handle portion 24.

Figures 9, 10, 11, 12:
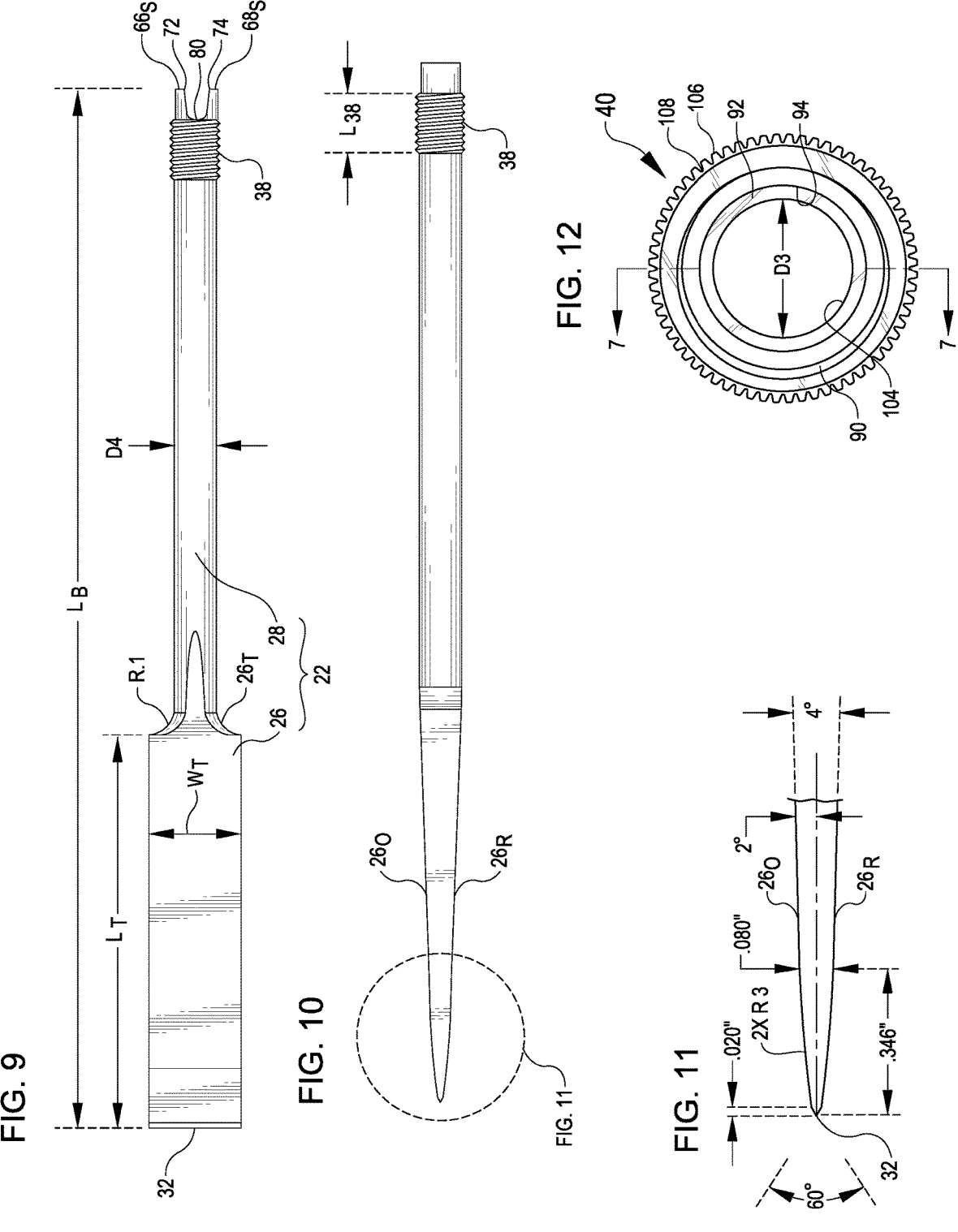
FIG. 9 is a plan view of an embodiment for a disposable blade portion of an osteotome, taken looking down on the blade portion, showing the blade portion oriented as depicted in FIGS. 6 and 7 above.
FIG. 10 is a side elevation view of an embodiment for a disposable blade portion of an osteotome, as just illustrated in FIG. 9 above, now showing a look at the side of the blade portion, showing the blade portion and the blade shaft portion, as well as an externally threaded portion on the blade shaft portion.
FIG. 11 is a detailed side view of the sharp distal end of the blade portion, and adjacent areas of the blade portion, in the blade portions identified by line 11-11 of FIG. 10, when an osteotome blade design is provided.
FIG. 12 is an end view of an embodiment for a coupler, showing the generally tubular cylindrical structure with a threaded internal sidewall, as well as the retaining portion which is configured to slide along the handle shaft portion, yet be retained by the retainer near the distal end of the handle shaft portion.

As seen in FIG. 7 and in FIG. 12, the coupler 40 may include cylindrical portion 86 having an interior 88 which is at least partially threaded using threads 90. In an embodiment, a coupler 40 may additionally include a retaining portion 92. The retaining portion 92 may be provided in the form of cylindrical opening defined by interior sidewall 94. In an embodiment, the coupler 40 maybe sized and shaped for sliding engagement along a an unthreaded portion of the handle shaft portion 44. The coupler 40 may be retained on the handle shaft portion 44 by interference between a retainer 96 on handle shaft portion 44 and the retaining portion 92. In an embodiment, retainer 96 may be provided at or near the first distal end 46 of the handle shaft portion 44. In an embodiment, the retainer 96 may be provided in the form of a ringlike structure outwardly protruding from the handle shaft portion 44. In an embodiment, a seat 98 may be provided in coupler 40 for the retainer 96, so that the retainer 96 is received in mating engagement in the seat 98. For securely joining the handle portion 24 to the blade portion 22, the coupler 40 may be sized and shaped for complementary threaded engagement with the externally threaded portion 38 of the blade shaft portion 28. Thus, upon tightening of the coupler 40 as shown in FIG. 7, between threads 90 and exterior threaded portion 38, the blade shaft portion 28 is secured to handle shaft portion 44.

As seen in FIG. 13, in an embodiment, the handle shaft portion 44 may be configured having a cylindrical portion 100. In an embodiment the cylindrical portion 100 has a diameter D1. As seen in FIGS. 3 and 13, in an embodiment, diameter D1 may be zero point two five (0.250) inches (about six point three five (6.35) millimeters). As also seen in FIGS. 3 and 13, retainer 96 may be provided in the form of a ringlike structure having a diameter of D2 (see FIG. 15), which extends at least in part radially outwardly from the cylindrical portion 86 of handle shaft portion 44. In an embodiment, diameter D2 may be about zero point three one zero (0.310) inches, i.e. seven point eight seven four (7.874) millimeters. Thus, as seen in FIG. 13, diameter D2 (of the retainer 96) is greater than diameter D1 (of the cylindrical portion 86 of handle shaft portion 44).

Figure 8:
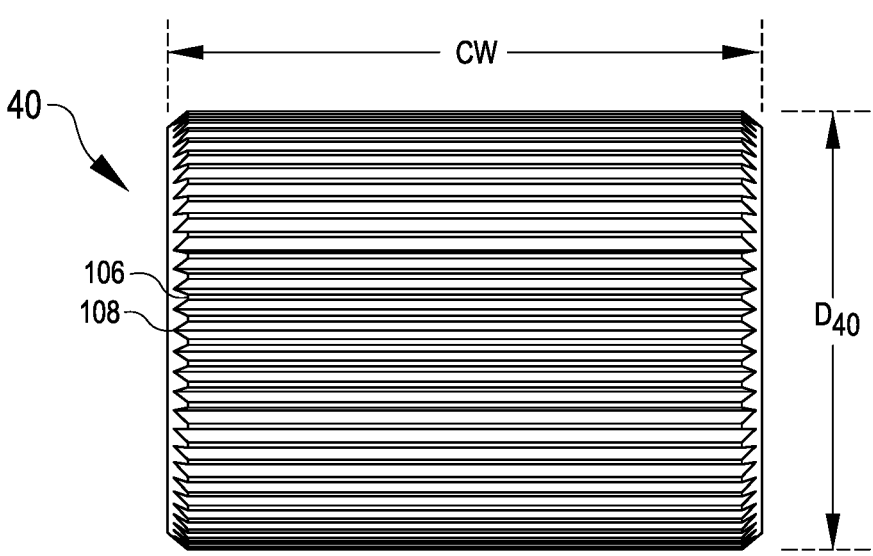
FIG. 8 provides a side view of an embodiment for a coupler, showing the use of grooves and ridges to provide an ergonomical design for this particular service, to allow a firm and safe grip by a user's hand on the coupler during tightening and untightening as necessary for replacement of blade portions.

As seen in FIG. 7, the retaining portion 92 of the coupler 40 comprises an interior surface 104 having a diameter D3. The diameter D3 is greater than diameter D1 but less than diameter D2. As noted in FIG. 8, in an embodiment, the coupler 40 may be provided with a coupler width CW of about zero point six seven five (0.675) inches (i.e. seventeen point one four five (17.145) millimeters). Additionally, in an embodiment, the coupler 40 has an exterior surface that includes gripping features. In an embodiment, the gripping features are provided in the form of ridges 106 and grooves 108.

In various embodiments, the longitudinally extending base 30 of the blade portion 22 may include a prism shaped portion 110. In an embodiment, the prism shaped portion 110 may be tapered from a thickness of TP to a thickness of TD, along at least a portion of a longitudinal axis thereof.

In various embodiments, the sharp distal end 32 may be provided having a selected width W. In an embodiment, the sharp distal end 32 may be between about two (2) millimeters (about zero point zero seven nine (0.079) inches) to about twenty five (25) millimeters (about zero point nine eight four (0.984) inches), or if sized in English units, to about twenty five point four (25.4) millimeters (about one (1) inch). In an embodiment, the sharp distal end 32 may be provided having a selected width between about two (2) millimeters (about zero point zero seven nine (0.079) inches) to about thirty one point seventy five (31.75) millimeters (about one and one point two five (1.25) inches).

A surgical instrument system has thus been described where a replaceable end effector may be provided as required for use in each surgery or in each new procedure during surgery. In an embodiment, the replaceable end effector may be an osteotome. In an embodiment, the replaceable end effector may be a chisel. For illustrative purposes, see FIG. 11, which shows that osteotomes may be provided having a beveled surface leading toward the sharp distal end 32 on both an obverse side 260 and on a reverse side 26R of tool edge portion 26. On the other hand, a chisel design used as a replaceable end effector would include a beveled surface leading toward the sharp distal end 32 only on the obverse side 260.

As seen in FIG. 9, in an exemplary embodiment, the blade portion 22 may be provided having an overall length $L_B$ of about six point two four (6.24) inches (about one hundred fifty eight point five (158.5) millimeters). In an exemplary embodiment, the tool end portion 26 (excluding tapered portions 26T at the proximal end) may be provided having an overall length LT of about two point three five (2.35) inches (about fifty nine point sixty nine (59.69) millimeters). In various embodiments, the width WT of the tool edge portion 26 may be the same, or approximately the same, as the range of widths W noted herein for the sharp distal end 32. In various embodiments, diameter D4 of the blade shaft portion 28 may be about zero point two five zero (0.250) inches (about six point three five (6.35) millimeters. As noted in FIG. 10, in an embodiment, the length $L_{38}$ of threaded portion 38 on the blade shaft portion 28 may be about zero point three seven five (0.375) inches (about nine point five two five (9.525) millimeters.

A surgical instrument system may be provided in the form of a kit, wherein at least one handle portion 24 including a coupler 40 is provided, and a plurality of blade portions 22 are provided. In such a kit, the coupler 40 may be adapted for sliding movement along a handle shaft portion 44 and yet be retained on the handle portion 44 by an interference fit between a retainer 96 and a retaining portion 92 as described in detail above. And the coupler 40 may be adapted for threaded engagement with externally threaded portion 38 on a blade portion 22 as described above. A plurality of blade portions 22 may be provided in such a kit. Each of the blade portion 22 may be configured for secure locking engagement with the and at least one handle portion 24, and may be secured thereto by tightening the coupler 40, to thereby secure the at least one handle portion 24 to a selected blade portion 22. The blade portions 22 may be of varying design, i.e. osteotome, or chisel, as noted above. The blade portions 22 may be provided in a variety of sizes, i.e. in a variety of widths W at the sharp distal end 32. And, kits may be provided with a plurality of blade portions 22 having the same width W at their sharp distal end 32. For example, a single handle portion 24 may be provided in a kit having a dozen (12) blade portions 22 of the same width W. Or, a single handle portion may be provided in a kit having a dozen (12) blade portions 22, each having a different width W. And, variations in kit configurations may be expected depending on the usage of specific blade portions by surgeons in their work on patients.

In summary a novel design for a surgical instrument system has been described herein. In an embodiment, the surgical instrument system may provide new design which enables replacement of the cutting edge blades in osteotomes. The designs provided herein are structurally solid, longitudinally, providing steel-to-steel contact from a striking plate 54 (where they may struck by a mallet) to the cutting edge at the sharp distal end 32. An easily manually manipulated connection mechanism is provided, which is simple, and sturdy (no wiggle). Further, the design assures that the coupler 40 does not obstruct the view of the surgeon of the tip (i.e. the sharp distal end 32) of the osteotome 20. In an embodiment, minimizing the diameter $D_{40}$ of the coupler 40, as compared to the diameter D1 of the handle portion 42, is advantageous. Basically, the diameter $D_{40}$ of coupler 40 should be less than the diameter D1 of handle portion 42, and in an embodiment $D_{40}$ should be about fifty percent (50%) or so of the diameter D1 of the handle portion 42. In any event, the disposable nature of the blade portions 22, and the solid connection system described herein, will make it cost effective to use a new, safe osteotome blade for each new surgery.

In summary, the surgical tool system described herein is a novel system for providing replaceable cutting edges or other tools, and especially for replacing cutting tools such as osteotomes or chisels, in order to assure that sharp cutting instruments are available to surgeons for each new procedure. The surgical tool system described herein makes available a variety of new, high quality blade portions for use with an existing handle portion, to both assure sharp tools, while minimizing cost of blade portion replacements.

It is to be appreciated that the surgical tool system with replaceable blade portions and reusable handle portions, as described herein, is an appreciable improvement in the art. The embodiments have been thoroughly described to enable those of ordinary skill in the art to make and use the invention, including embodiments which utilize a steel-to-steel impact/force pathway, and which include anti-rotation elements in a joint between the blade portion and the handle portion, for reliable yet replaceable blade portion use.

Although only a few exemplary elements of embodiments have been described in detail, various details are sufficiently set forth in the drawings and in the specification provided herein to enable one of ordinary skill in the art to make and use the invention(s), which need not be further described by additional writing in this detailed description. It will be readily apparent to those skilled in the art that the surgical tool systems, including osteotomes with replaceable blades, may be modified from those embodiments provided herein, without materially departing from the novel teachings and advantages provided.

The aspects and embodiments described and claimed herein may be modified from those shown without materially departing from the novel teachings and advantages provided by this invention, and may be embodied in other specific forms without departing from the spirit or essential characteristics thereof.

The embodiments presented herein are to be considered in all respects as illustrative and not restrictive. As such, this disclosure is intended to cover the structures described herein and not only structural equivalents thereof, but also equivalent structures. Numerous modifications and variations are possible in light of the above teachings. It is therefore to be understood that within the scope of the appended claims, the invention(s) may be practiced otherwise than as specifically described herein. Thus, the scope of the invention(s), as set forth in the appended claims, and as indicated by the drawing and by the foregoing description, is intended to include variations from the embodiments provided which are nevertheless described by the broad interpretation and range properly afforded to the plain meaning of the claims set forth below.

The invention claimed is:

1. An osteotome, comprising:
   a blade portion and a handle portion, the blade portion and the handle portion comprising separable components;
   the blade portion comprising a tool edge portion and blade shaft portion, the tool edge portion comprising a longitudinally extending base extending outward to a sharp distal end, the blade shaft portion extending between a proximal end of the longitudinally extending base and a first proximal end of the blade shaft portion, and adjacent the first proximal end, an externally threaded portion:
   the handle portion comprising a hand grip portion and a handle shaft portion, the handle shaft portion extending between a proximal end adjacent the hand grip portion and a first distal end, and a retainer, the retainer comprising a lip outwardly protruding from the handle shaft portion;
   wherein the first proximal end further comprises a first end piece, and wherein the first distal end comprises a second end piece, and where the first end piece and the second end piece are designed for interlocking engagement that prevents rotation therebetween; and
   a coupler, the coupler comprising (a) a cylindrical portion having an interior which is at least partially threaded, and (b) a retaining portion, the coupler sized and shaped for sliding engagement along an unthreaded portion of the handle shaft portion,
   wherein the coupler is retained on the handle shaft portion by interference between the retainer and the retaining portion;
   wherein the coupler is sized and shaped for threaded engagement with the externally threaded portion of the blade shaft portion and upon tightening thereby secures the handle portion to the blade portion; and
   wherein the first end piece on the blade portion comprises (a) a pair of circular segments oriented transversely to a longitudinal axis of the blade shaft portion, and (b) a gullet between the pair of circular segments, the gullet sloping inwardly and extending distally along the longitudinal axis of the blade shaft portion.

2. The osteotome of claim 1, wherein the second end piece on the handle shaft portion comprises a generally U-shaped protrusion, the generally U-shaped protrusion sized and shaped for secure interlocking engagement with the gullet in the first end piece.

3. The osteotome of claim 1, wherein the handle shaft portion comprises a cylindrical portion.

4. The osteotome of claim 3, wherein the cylindrical portion of the handle shaft portion has a diameter D1, and wherein the retainer comprises a hoop having a diameter D2, where the hoop extends outwardly from the cylindrical portion, wherein D2 is greater than D1.

5. The osteotome of claim 4, wherein the retaining portion of the coupler comprises an interior surface having a diameter D3, and wherein diameter D3 is greater than diameter D1 but less than diameter D2.

6. The osteotome of claim 1, wherein the coupler further comprises an exterior surface, and wherein the exterior surface further comprises grooves.

7. The osteotome of claim 1, wherein the longitudinally extending base of the blade portion comprises in part, a prism shaped portion, wherein the prism shaped portion is tapered from a thickness of TP to a thickness of TD, along at least a portion of a longitudinal axis thereof.

8. The osteotome of claim 1, wherein the sharp distal end has a selected width W.

9. The osteotome of claim 8, wherein width W is between about two (2) millimeters and about twenty five (25) millimeters.

10. A replaceable end effector for use with a surgical instrument system, the surgical instrument system including a reusable handle, the replaceable end effector comprising:
   a blade portion, the blade portion comprising a tool edge portion and a blade shaft portion, the tool edge portion comprising a longitudinally extending base extending outward to a sharp distal end, the blade shaft portion extending between a proximal end of the longitudinally extending base and a first proximal end of the blade shaft portion, and adjacent the first proximal end, an externally threaded portion;
   wherein the first proximal end further comprises a first end piece having an anti-rotation element configured for interlocking engagement with the reusable handle; and
   wherein the first end piece comprises (a) a pair of circular segments oriented transversely to a longitudinal axis of the blade shaft portion, and (b) a gullet between the pair of circular segments, the gullet sloping inwardly and extending distally along a longitudinal axis of the blade shaft portion.

11. The replaceable end effector as set forth in claim 10, wherein the longitudinally extending base of the blade portion comprises, in part, a prism shaped portion, wherein the prism shaped portion is tapered from a thickness of TP to a thickness of TD, along at least a portion of a longitudinal axis thereof.

12. The replaceable end effector as set forth in claim 10, wherein the blade portion comprises an osteotome.

13. The replaceable end effector as set forth in claim 10, wherein the blade portion comprises a chisel.

14. The replaceable end effector as set forth in claim 10, wherein the sharp distal end has a selected width W.

15. The replaceable end effector as set forth in claim 14, wherein width W is between about two (2) millimeters and about twenty five (25) millimeters.

16. The replaceable end effector as set forth in claim 14, wherein width W of the sharp distal end is between about two (2) millimeters and about thirty one point seventy five (31.75) millimeters.

17. A surgical instrument kit, comprising:
   a plurality of blade portions, and at least one handle portion, wherein the plurality of blade portions are configured for being individually detachably coupled to one of the at least one handle portion;

wherein at least some of the plurality of blade portions comprise a tool edge portion and blade shaft portion, the tool edge portion comprises a longitudinally extending base extending outward to a sharp distal end, the blade shaft portion extends between a proximal end of the longitudinally extending base and a first proximal end of the blade shaft portion, and adjacent the first proximal end, an externally threaded portion;

wherein at least one handle portion comprises a hand grip portion and a handle shaft portion, and wherein the handle shaft portion extends between a proximal end adjacent the hand grip portion and a first distal end, and a retainer, the retainer comprising a lip outwardly protruding from the handle shaft portion; and wherein the first proximal end further comprises a first end piece, and wherein the first distal end further comprises a second end piece, and, wherein the first end piece comprises an anti-rotation element configured for interlocking engagement with the reusable handle, and wherein the first end piece comprises (a) a pair of circular segments oriented transversely to a longitudinal axis of the blade shaft portion, and (b) a gullet between the pair of circular segments, the gullet sloping inwardly and extending distally along a longitudinal axis of the blade shaft portion, so that engagement between the first distal end and the gullet prevents rotation between the blade shaft portion and the handle portion.

18. The kit as set forth in claim 17, wherein each of the at least one handle portion further comprises a coupler, the coupler comprising (a) a cylindrical portion having an interior which is at least partially threaded, and (b) a retaining portion, the coupler sized and shaped for sliding engagement along an unthreaded portion of the handle shaft portion, and wherein the coupler is retained on the handle shaft portion by interference between the retainer and the retaining portion; and wherein the coupler is sized and shaped for threaded engagement with the externally threaded portion of a selected blade shaft portion, and upon tightening thereby secures a handle portion to a selected blade portion.

19. The kit as set forth in claim 17, wherein the longitudinally extending base of each one of the plurality of blade portions comprise a prism shaped portion, wherein the prism shaped portion is tapered from a thickness of TP to a thickness of TD, along at least a portion of a longitudinal axis thereof.

20. The kit as set forth in claim 17, wherein the sharp distal end has a selected width W.

21. The kit as set forth in claim 20, wherein width W is between about two (2) millimeters and about thirty one point seven five (31.75) millimeters.

22. The kit as set forth in claim 17, wherein at least some of the plurality of blade portions comprise an osteotome.

23. The kit as set forth in claim 17, wherein at least some of the plurality of blade portions comprise a chisel . . .

* * * * *